United States Patent [19]

Wildman et al.

[11] 4,347,324
[45] Aug. 31, 1982

[54] PROCESS FOR ISOLATION OF PROTEINS FROM PLANT LEAVES

[75] Inventors: Samuel G. Wildman, Santa Monica, Calif.; Prachuab Kwanyuen, Gary, N.C.

[73] Assignee: Leaf Proteins, Inc., Raleigh, N.C.

[21] Appl. No.: 264,116

[22] Filed: May 15, 1981

Related U.S. Application Data

[63] Continuation-in-part of Ser. No. 78,505, Sep. 24, 1979, Pat. No. 4,268,632.

[51] Int. Cl.$^3$ .............................................. C12N 9/88
[52] U.S. Cl. ..................................... 435/232; 435/816
[58] Field of Search ................ 435/232, 816; 426/655; 260/112 R

[56] References Cited

U.S. PATENT DOCUMENTS

| | | | |
|---|---|---|---|
| 2,600,903 | 6/1932 | Miller | 426/655 X |
| 3,780,183 | 12/1973 | Edwards et al. | 426/655 X |
| 3,823,128 | 7/1974 | Bickoff et al. | 426/655 X |

OTHER PUBLICATIONS

Kung et al., in Methods in Enzymology, vol. 69, pp. 326–336, (1980).
Chan et al., Science, vol. 176, pp. 1145–1146, (1972).
Johal et al., Science, vol. 204, pp. 75–77, (Apr. 1979).

*Primary Examiner*—Lionel M. Shapiro
*Attorney, Agent, or Firm*—Lyon & Lyon

[57] ABSTRACT

Described herein is a process for isolating the enzymatic protein ribulose 1,5-diphosphate carboxylase from the green leaves of plants. In the process, which is particularly suited to obtaining the protein from tobacco, the leaves are ground or otherwise pulverized in the presence of a reducing agent. A liquid portion containing the desired protein is separated from the pulp and its pH adjusted to within the range of from about pH 6.0 to 5.3 and then cooled to cause the crystallization of the ribulose 1,5-diphosphate carboxylase. After separation of the crystalline material, the supernatant is acidified to yield lower molecular weight proteins.

24 Claims, No Drawings

PROCESS FOR ISOLATION OF PROTEINS FROM PLANT LEAVES

CROSS REFERENCE TO RELATED APPLICATIONS

This application is a continuation-in-part of our copending application Ser. No. 78,505, filed Sept. 24, 1979, now U.S. Pat. No. 4,268,632, issued May 19, 1981, the disclosure of which is incorporated by reference.

FIELD OF THE INVENTION

In a broad aspect this invention relates to a process for isolating proteins from plant leaves. In another aspect it relates to a process for obtaining ribulose 1,5-diphosphate carboxylase from the green leaves of plants. In another, and more specific aspect, it relates to a process for obtaining ribulose 1,5-diphosphate carboxylase from tobacco leaves.

BACKGROUND

The succulent leaves of certain plants, including tobacco, spinach, soybeans, wheat, cotton and alfalfa, are composed of 10–20% solids, the balance being water. For its parts, the solid portion is composed of a water soluble portion and a water insoluble portion, the latter being made up, for the most part, of the fibrous structural material of the leaf.

The water soluble compounds are divisible into two groups. One group includes compounds of relatively lower molecular weight such as sugars, vitamins, amino acids and other compounds whose molecular weight do not exceed about 10,000. The second group is almost exclusively proteins whose molecular weights are about 30,000 or greater.

The proteins can be resolved into two fractions. One fraction contains a mixture of proteins whose molecular weights range from about 30,000 to 100,000. These proteins are sometimes referred to as "Fraction 2 proteins." The remaining fraction comprises a single protein having a molecular weight of about 550,000 and is sometimes referred to as "Fraction 1 protein."

Fraction 1 protein was first identified in 1947. Subsequent research led to the discovery that this protein was an enzyme involved in photosynthesis. Since then it has been given a number of names. Among these are ribulose 1,5-diphosphate carboxylase, carboxydismutase, ribulose 1,5-bisphosphate carboxylase and ribulose 1,5-di(or bis) phosphate carboxylase-oxygenase.

Fraction 1 protein may compose up to 25% of the total protein content of a leaf and up to 10% of the solid matter in the leaf. In 1970 it was discovered that crystalline Fraction 1 protein could be obtained from tobacco leaves.

Fraction 1 protein, when pure, is odorless, tasteless and colorless and has high nutritional value. In view of these properties, and because it can be obtained in high purity, Fraction 1 protein is considered to have a potentially valuable application as a food supplement for animals and humans. In the case of humans, the additive could be a component of high protein or other special diets. It has, for example, been suggested as a supplement to the diet of persons who require dialysis because of kidney disease.

Despite its relative abundance in cultivated plants, Fraction 1 protein is not a commercially important product since the processes known to the art for obtaining it from vegetable matter are not commercially feasible.

Three basic processes for isolating Fraction 1 protein have been described in the published literature. Each published method begins with pulping the leaves, or leaves and stalk of the plant, followed by expressing a green juice from the pulp. The green juice, which contains finely particulate green pigmented material, is clarified for example, by filtration or centrifugation, to separate the finely particulate solid matter from the liquid. The resulting liquid is brown in color.

The first method described for isolating Fraction 1 protein involved concentration of Fraction 1 protein simultaneously with its partial separation from lower molecular weight compounds in the brown juice by molecular filtration. Using a molecular sieve whose pores would pass smaller molecules without passing Fraction 1 protein, the brown juice was placed under pressure so that small molecules would pass through the pores.

The solution containing the Fraction 1 protein was concentrated about ten-fold and then dialyzed to remove additional small molecules in the solution. Dialysis was accomplished using a collodion type dialysis bag. The pores of the bag would not permit passage of the Fraction 1 protein but allowed the smaller molecules to escape through the bag into water. During dialysis, crystals of Fraction 1 protein formed.

The second method developed to isolate the Fraction 1 protein involved passing the brown juice obtained from the leaves through a Sephadex chromatographic column. Sephadex consists of water insoluble microscopic beads of polymerized sugar. Either Sephadex G-25 or G-50 was used to perform the separation. Selection of proper beads permits small molecules to penetrate to the interior of their structure to the exclusion of larger molecules. The larger molecules, therefore, are only found in the liquid in the interstices between the tightly packed Sephadex beads. This interstitial space is referred to as the "void volume".

To achieve effective separation, the volume of brown juice cannot exceed about 25% of the total volume of the beads. The beads are first equilibrated with a buffer and a volume of brown juice, containing the same buffer, is then layered on top of the Sephadex column.

The brown liquid is eluted from the column using the buffer solution. As the juice moves down the column, the passage of small molecules is retarded since they penetrate the interior of the beads. The large Fraction 1 molecules, on the other hand, move at a faster rate down the column through the labyrinth formed by the interstices between the beads and emerges from the column as a clear brown solution. However, elution results in at least two-fold dilution of the solution. Removal of the smaller molecules changes the environment around the molecules of Fraction 1 protein which leads to crystallization.

The most recently described method provides passage of the brown juice through a Sephadex G-25 column as described above. If Fraction 1 protein does not crystallize, as is the case with the extract of all plants except tobacco, ammonium sulfate is added until the solution is 30–50% saturated. This leads to precipitation of an amorphous material which is collected by centrifugation. After separation, the precipitate is redissolved in a smaller volume of buffer than that from which it was precipitatd to which is added 8% polyethylene glycol. This mixture is placed in an open dish adjacent to another open dish containing silica gel and the two dishes confined in a closed vessel. Water is gradually evaporated from the protein solution and absorbed by the silica gel. With the passage of time, crystals of Fraction 1 protein develop.

It will be clear to those skilled in the art that the prior art processes described above are either time consuming, expensive or both. However, in our copending application Ser. No. 78,505, we describe a simple process for isolating Fraction I protein comprising the steps of converting the leaves to a pulp, heating the liquid portion of the pulp to a temperature below that which causes the protein to denature followed by cooling the liquid portion to a temperature at which Fraction 1 protein, i.e., ribulose 1,5-diphosphate carboxylase crystallizes.

SUMMARY OF THE INVENTION

Since making the invention described in our copending application Ser. No. 78,505, we have discovered an even simpler and more efficient process for isolating ribulose 1,5-diphosphate carboxylase from the leaves of green plants. In that regard, we have discovered that the heating step which we originally believed to have been an essential part of the process can be eliminated in most cases. By our improved process, ribulose 1,5-diphosphate carboxylase is obtained in crystalline form by adjusting the pH of the liquid portion of a pulp derived from the leaves to a value in the range of from between about 6 to a pH above that at which the protein will denature and precipitate as an amorphous mass, i.e., to a value above the isoelectric point which occurs at about pH 5.0. The liquid, after separation of insoluble material, is then permitted to stand, preferably while cooled below ambient temperature, to permit crystallization of the Fraction 1 protein. It has been our general observation that crystallization occurs more readily as the pH decreases, i.e., nears the isoelectric point.

As object of this invention is to provide an improved process for the isolation of Fraction 1 protein.

Another object is to obtain Fraction 1 protein in high yield and purity.

The manner in which these and other objects are accomplished by the present invention is described in the following detailed description of the invention.

DETAILED DESCRIPTION OF THE INVENTION

The process of the present invention may be used to isolate ribulose 1,5-diphosphate carboxylase and lower molecular weight protein from leaves of many varieties. However, because tobacco leaves, and particularly the leaves of immature tobacco, are a particularly rich source of the protein, it is preferred to use such leaves in the process of the invention. Accordingly, the invention will be described with specific reference to the isolation of ribulose 1,5-diphosphate carboxylase from tobacco.

After detachment of the leaves from the tobacco plant, the leaves, or leaves and stalk together if small plants are the source of the leaves, are ground, crushed or otherwise reduced to a pulp to release the liquid portion of the leaves from the solids. Preferably, the pulping process is carried out in the presence of a reducing agent. In that regard, the pulping process permits phenol oxidase enzymes present in the leaves to contact the leaf proteins. This results in oxidation of aromatic amino acids such as tyrosine which comprise part of the primary structure of proteins. This oxidation modifies the protein, made visually manifest by their becoming brown, and lowers their solubility in water. The reducing agent, in effect, acts as an antioxidant to suppress this oxidation.

The presently preferred reducing agent for use in the invention is 2-mercaptoethanol because it is volatile and evaporates during the further processing described below leaving little or no residue in the material isolated. However, other reducing agents may also be used. Among these are agents such as sodium metabisulfite and dithiothreitol. Separation of the residue of these agents, if any, can be done using conventional techniques. The amount of reducing agent sufficient to control the oxidation can vary depending, for example, on the agent selected. In the case of 2-mercaptoethanol, effective suppression of the undesirable oxidation can be achieved using about 5 milliliters of the liquid agent per kilogram of plant material being processed.

The liquid portion of the plant material contains the plant proteins, including Fraction 1, and other solids in dissolved form. The solid portion of the pulp includes coarse, easily separated material and finally particulate green pigmented material which is difficult to separate from the liquid. The coarse material is preferably separated from the liquid portion promptly after the leaf material is converted to a pulp. A simple filtration, for example, using cheese cloth, will accomplish this separation. When this is done, the liquid portion which still contains the finely particulate, green pigmented material is treated with acid, preferably hydrochloric acid, as necessary, to bring the pH to within the desired range, i.e., to within the range from about pH 6.0 to a point near but above the isoelectric point at which the protein in the liquid portion is denatured whereby it precipitates as an amorphous mass. This mass contains both Fraction 1 and Fraction 2 protein material. The isoelectric point of proteins is at about pH 5.0. Therefore, the practical lower limit to which the pH should be adjusted according to the present invention is about pH 5.3. Separation of the coarse material may be carried out after acidification of the liquid. Other mineral acids including phosphoric and sulfuric may also be used.

We have found that the pH of the liquid portion of tobacco leaf pulp varies according to the age of the plant. In the case of very young plants, i.e., plants less than about 12" tall, the pH will be in the range of about 6.0 or higher. As the plants mature, the pH of the liquid portion decreases, i.e., the liquid portion is naturally more acidic. For example, the pH of liquid from plants in the range of from 18" to 24" in height was about pH 5.7, whereas the liquid portion derived from plants 24" to 36" had a pH of about 5.3.

For best results, preferably the pH of the liquid portion is adjusted to a range from about 5.4 to 5.8, most preferably to a pH of about 5.4–5.6. When the pH is above about 5.8, crystallization occurs at a significantly slower rate than at a lower pH. By contrast, when the pH is adjusted to below about 5.4, the Fraction 1 protein which is obtained has lost desirable properties. We believe that adjusting the pH to near the isoelectric point causes changes in the Fraction 1 protein akin to those which result from its denaturation. For example, it is more difficult to redissolve Fraction 1 protein which crystallizes from a liquid at pH below about 5.4.

We have also found that by adjustment of the pH to within the preferred range 5.4–5.6, the separation of the finely particulate green material is facilitated as it partially coagulates. This material, which contains the plant chlorophyll, can be separated by any suitable means but centrifugation is a convenient and preferred way to do so.

In some cases, particularly in the case of pulp material from more mature plants or if a pH above about 5.6 is used, it may be necessary to heat the mixture containing finely particulate green material to obtain easy separation. The heating step has the effect of coagulating the finely particulate material to an extent that permits its separation by centrifuging as discussed above.

The entire pulp may be heated to facilitate separation of the green finely particulate material. However, it is preferred to heat the portion of the pulp remaining after the coarse material is removed.

The heating step must be carried out at a temperature below that at which the protein will denature by heat alone. Generally, therefore, the heating step should be carried out below about 52° C. as heating above that temperature results in precipitation of the protein. We have obtained good results by heating the pulp to about 48° C. (118° F.) for not more than about 15 minutes. Temperatures below about 48° C. can be used but longer heating times are required.

The heat treatment can be performed either as a continuous or batch process as described in our copending application Ser. No. 78,505. Thus, in a batch process, the pulp is placed in a vessel whereby heat is transferred to the pulp under conditions where no part of the pulp, or at least the liquid portion thereof, is heated to a temperature at which the protein denatures. As indicated above, preferably the pulp is heated to a temperature of 50°±1° C. for from about 15 minutes to about 20 minutes.

In a continuous process, the pulp is pumped without undue agitation through coils immersed in a liquid heated to a temperature such that, by heat exchange, a specified volume of pulp would be heated to 50° C.±1° C. for from about 15 minutes to about 20 minutes and then through coils in contact with liquid at a temperature lower than 50° C. to reduce the temperature of the pulp.

Heating the pulp as described above to cause coagulation of the finely particulate material is more efficient than merely adjusting the pH. However, the heating regimen should be used only if necessary to remove the finely particulate material since it has the actual effect of increasing the time over which crystallization of the Fraction 1 protein occurs and, in some cases, the amount of protein obtained.

As indicated, the finely particulate material can be separated after coagulation, for example, by centrifugation, from the liquid portion. The supernatant liquid obtained is a brown juice. This juice is stored at a temperature at which crystallization will occur, usually at or below room temperature to obtain crystals of Fraction 1 protein. We have obtained particularly good results by cooling the brown juice to about 8° C. The maximum storage time required is not more than about 16 hours. It has been our experience that storage beyond 16 hours does not usually improve yields. The crystallized ribulose 1,5-diphosphate carboxylase is separated from the supernatant liquid by filtration or centrifugation (3000 RPM, 5 min.).

The crystalline form of ribulose 1,5-diphosphate carboxylase differs from the three forms obtained using prior art processes. Form I crystals have the shape of dodecahedrons and are produced by the previously mentioned processes using molecular sieves or Sephadex chromatography. Form II crystals have the shape of extremely thin plates and so far have been produced only under very special conditions and in extremely small amounts for x-ray crystallographic studies. Form III crystals are tetragonal bipyramids and are produced by the ammonium sulfate and polyethylene glycol treatment previously mentioned.

By contrast, the Fraction 1 protein crystals produced by the process described herein take yet a fourth form, unlike the other three forms of crystals known to the art. Thus, using the process of the present invention, Fraction 1 protein crystals are obtained having an apparent octagonal form, by microscopic examination, in high yield and in high purity.

In contrast to Form I crystals which will redissolve in water containing common salt (NaCl), the octagonal crystals remain undissolved but will generally go into solution when the crystals are suspended in water adjusted to pH 7.5 or higher by sodium hydroxide (NaOH). We have found that the protein obtained from very mature plants, i.e., those 24" to 36" in height whose brown juice has a pH of 5.3 naturally, may not redissolve in water (pH 8.5 by the addition of NaOH). Dialysis of the redissolved Fraction 1 protein against a buffer (tris, pH 7.5) followed by passage through a Sephadex column will cause recrystallization, but now as Form I crystals.

The Fraction 1 crystals obtained from the brown juice can be conveniently purified by washing with water to remove contaminants. Separation of the crystals from the supernatant is again best achieved by centrifuging. Low speed centrifugation (~3,000 RPM) for five minutes will suffice.

This process of crystallization of the Fraction 1 protein will result in its substantially complete removal from the brown juice. The resulting supernatant contains Fraction 2 proteins, other soluble solids and uncrystallized Fraction 1 protein, if any. Fraction 2 protein may be removed from the supernatant by acidifying it to at or below the isoelectric point, i.e., to a pH of 5.0 or below. This causes the proteins in solution to precipitate. Highest yields of protein are obtained by adjusting the pH to about 4.0–4.5 by the addition of hydrochloric acid or other suitable acids. The resulting precipitate can be collected by centrifugation (3000 RPM, 5 min.). Contaminants can be removed if the precipitate is washed with water and again collected by centrifugation.

The passage of time between harvesting the leaves, converting them to a pulp (which may be by grinding, crushing or any other suitable process), adjusting the pH, performing the heating step, if necessary, and separation of solid material from the liquid portion should be accomplished as soon after harvesting as possible. Delays in accomplishing these steps reduces the yield of ribulose 1,5-diphosphate carboxylase that can be obtained. Therefore, it is preferred to perform these operations at or near the site where the leaves are harvested.

The following examples provide further details of the invention.

EXAMPLE 1

Type NC95 tobacco plants are cultivated at a plant density of 0.5 square feet per plant until a height of 18–24 inches is attained. The plants are cultivated in such a way that the leaves are deep green in color. The entire aerial portions of the plants are harvested and cut into pieces small enough to be introduced into a one gallon size Waring blender. The blades of the blender are covered with about 200 ml. of water. (The Waring blender will not disintegrate the plant material unless the blades are submerged in a liquid. However, with other such devices, such as a Rietz disintegrator, addition of water would be unnecessary.)

A one kilogram batch of coarsely chopped stems and leaves obtained from the harvested plant material is added to the water with 5 ml. of 2-mercaptoethanol and blended to a smooth pulp. The resulting pulp, which has the consistency of a thick pancake batter, consisting of a volume of about 1.2 liters. The coarse material in the pulp was poured onto two layers of 24/20 mesh cheese cloth supported on a 8 inch diameter, 32 mesh sieve which is placed in a large funnel draining into a collecting flask.

Processed in this way, the 1.2 liters of pulp yields approximately 1.0 liter of liquid containing green pigmented material. The "green juice" had a pH of from about 5.7 to 5.9 in different preparations.

The green juice was divided into equal aliquots of 500 ml each. One aliquot was kept at 25° C. while the other was heated to 50° C. for 10 minutes. Then both aliquots were simultaneously centrifuged in a Beckmann Ultra Centrifuge in an R-21 rotor at 18000 RPM for 30 minutes. This high centrifugal force removed all of the green color as a precipitate leaving a clear "brown juice". Each aliquot of brown juice, i.e., the heated and unheated aliquots, was divided into equal parts, one part stored at 8° C. and the other allowed to stand at 25° C. Equal amounts of Fraction 1 protein crystallized from each aliquot. Crystallization was complete in all cases within 16 hours, although crystals appeared more rapidly where the brown juice was refrigerated. This example demonstrates that heating of the liquid portion was not essential to obtaining the crystals of ribulose 1,5-diphosphate carboxylase.

EXAMPLE 2

Using the procedure of Example 1, a green juice having a pH of 5.7 was obtained from tobacco plants 18" to 24" in height. The green juice was divided into two equal portions. The pH of one portion was adjusted to pH 6.2 using sodium hydroxide. Both portions were heated to 50° C. for 10 minutes to facilitate removal of the finely particulate green material using moderate centrifugation. After removal of the green material, the two samples of brown juice were stored at 8° C. Within a few hours, crystals appeared in the brown juice of pH 5.7. No crystals appeared in the sample having pH 6.2 even after 24 hours.

In a similar experiment, brown juice derived from tobacco plants 24" to 36" in height having a pH of 5.3 produced crystals within 30 minutes and complete crystallization occurred within 3 hours after the first appearance of crystals. However, the resulting Fraction 1 protein would not redissolve at pH 8-8.5. In another experiment using tobacco plants 18" to 24" in height whose brown liquid was pH 5.8, crystals of Fraction 1 protein did not appear for 12 hours. Crystallization was complete within 16 hours. These data demonstrate that formation of crystals of Fraction 1 protein occurs more rapidly at lower pH.

EXAMPLE 3

Using the process of Example 1, a green juice was obtained from very young tobacco plants less than 12" tall. The juice obtained in this way had a pH of 6.0. The total juice obtained was divided into two equal parts and each part was subdivided into four equal aliquots for further processing. One aliquot from each of the original parts having a pH of 6.0 served as a control. An aliquot from each part was treated with hydrochloric acid to obtain a pH of 5.8; another was adjusted to pH 5.6 and another adjusted to pH 5.4. The four aliquots of one part were heated to 50° C. for 10 minutes. These four aliquots and the four aliquots from the other part were centrifuged to separate the finely particulate green material.

All the aliquots were permitted to stand at 8° C. to permit the formation of crystals of Fraction 1 protein. The time when crystals first appeared was noted and, when crystallization was complete, the amount of crystals obtained was noted. The brown juice was analyzed spectrophotometrically to determine the amount of finely divided green particulate matter contaminating the brown juice. The results are in Table I below.

TABLE I

| Condition of Green Juice | pH of Green Juice | Hours Before Appearance of Crystals | $\mu g/ml$ of Green Material in Brown Juice | mg/ml of Crystals of Protein From Brown Juice |
|---|---|---|---|---|
| Not heated | 6.0 | 8 | 10 | 6 |
| " | 5.8 | 6 | 5 | 6 |
| " | 5.6 | 3 | 1 | 6 |
| " | 5.4 | 3 | 0 | 6 |
| Heated to 50° C. | 6.0 | 48 | 0 | 3 |
| " | 5.8 | 48 | 0 | 3 |
| " | 5.6 | 16 | 0 | 5 |
| " | 5.4 | 3 | 0 | 6 |

These data further demonstrate that heating is not required to cause crystallization of Fraction 1 protein but, in fact, retards the rate of crystallization and decreases the amount of protein obtained in most cases. The effect of decreasing the pH is to clearly increase the rate at which crystallization occurs. Furthermore, whereas heating the samples facilitated the separation of the finely particulate green material, complete separation of the green material occurred for unheated samples whose pH had been adjusted to pH 5.4–5.6.

We have determined the efficiency of separation of Fraction 1 protein from green juice whose pH has been adjusted to the desired range by comparing the Schlieren patterns obtained from analytical centrifugation of the green juice and the brown juice after crystallization of the Fraction 1 protein. The former shows two well resolved peaks, one of which corresponds to Fraction 1 protein and the other to Fraction 2 proteins. In the latter, only a single peak corresponding to Fraction 2 proteins is observed. Since the analytical centrifugation method is capable of detecting as little as 0.1 mg/ml of Fraction 1 protein, it can confidently be stated that, after crystallization is complete, the concentration of Fraction 1 protein remaining in solution is less than 1%. By contrast, the mother liquid obtained from the prior art chromatography process using a Sephadex column contained, in addition to Fraction 2 proteins, about 30% of uncrystallized Fraction 1 protein.

From the foregoing description, it can be seen that the present invention provides a convenient process for obtaining protein, and especially Fraction 1 protein, from plant material. Thus, the process of the present invention obviates the need for costly and elaborate molecular filtration and Sephadex columns as required by prior art processes. Furthermore, no chemical agent is required other than the reducing agent which, in the case of 2-mercaptoethanol, evaporates during processing or is driven off in the heating step if used, in order to obtain the Fraction 1 protein and the acid used to adjust the pH of the liquid. Because it is unnecessary to dilute the liquid, recovery of Fraction 2 proteins is also simplified. Finally, after removal of the Fraction 2 proteins and uncrystallized Fraction 1 protein from the liquid portion, the liquid portion still contains low molecular weight compounds of value that can be more economically recovered than would be the case using the residue obtained by prior art processes since they are in their natural form and undiluted. By contrast, the residues obtained from prior art processes are contaminated by the chemicals used in the process and have been diluted during separation of the Fraction 1 protein which complicates further recovery. Our improved process also makes it unnecessary in most cases to use the heating regimen described in our copending application Ser. No. 78,505.

The invention has been described in terms of presently preferred embodiments. However, from the foregoing description of the invention, those skilled in the art will appreciate that modifications of the process can be made without departing from the scope of the invention which is to be limited only by the appended claims.

We claim:

1. A process for obtaining ribulose 1,5-diphosphate carboxylase from plant material comprising the leaves of green plants which process comprises the steps:
(a) converting the leaves to a pulp comprising a mixture of a solid portion and a liquid portion, said liquid portion containing dissolved ribulose 1,5-diphosphate carboxylase;
(b) adjusting, if necessary, the pH of the liquid portion to within the range of pH 6.0 to a pH sufficiently above the isoelectric point of the proteins in the liquid portion that said proteins do not precipitate;
(c) separating the liquid portion from the solid portion; and
(d) storing said liquid portion at a temperature at which said ribulose 1,5-diphosphate carboxylase crystallizes.

2. A process according to claim 1 wherein the crystals of ribulose 1,5-diphosphate carboxylase are separated from the liquid.

3. A process according to claims 1 or 2 wherein the plant material comprises the leaves of tobacco plants.

4. A process according to claims 1 or 2 wherein the pH is adjusted to within the range of pH 5.3–6.0.

5. A process according to claim 3 wherein the pH is adjusted to within the range 5.3–6.0.

6. A process according to claims 1 or 2 wherein the pH is adjusted to within the range 5.4–5.6.

7. A process according to claim 3 wherein the pH is adjusted to within the range of pH 5.4–5.6.

8. A process according to claim 2 wherein, after separation of ribulose 1,5-diphosphate carboxylase, the pH of the liquid portion is adjusted to a pH at or below the isoelectric point of dissolved proteins to precipitate said proteins.

9. A process according to claim 8 wherein the pH is adjusted to within the range 4.0–4.5.

10. A process according to claim 1 or 2 wherein the ribulose 1,5-diphosphate carboxylase crystallizes as octagonal crystals.

11. A process for obtaining ribulose 1,5-diphosphate carboxylase from tobacco plants comprising:
(a) converting the leaf portion of the plant to a pulp comprising a solid portion and a liquid portion, wherein said solid portion is comprised of coarse particulate material and finely particulate material and wherein said liquid portion contains dissolved ribulose 1,5-diphosphate carboxylase;
(b) adjusting, if necessary, the pH of the liquid portion to within the range of pH 6.0 to a pH sufficiently above the isoelectric point of the proteins in said liquid portion that the proteins do not precipitate;
(c) separating the liquid portion from the solid portion;
(d) storing the liquid portion at a temperature at which ribulose 1,5-diphosphate carboxylase crystallizes; and
(e) separating the ribulose 1,5-diphosphate carboxylase from the liquid portion.

12. A process according to claim 11 wherein the coarse particulate material is separated from the liquid portion prior to adjusting the pH.

13. A process according to claim 11 wherein the pH is adjusted prior to separation of said solid portion.

14. A process according to claims 11, 12 or 13 wherein the pH is adjusted to within the range 5.3–6.0.

15. A process according to claims 11, 12 or 13 wherein the pH is adjusted to within the range 5.4–5.6.

16. A process according to claims 11, 12 or 13 wherein the pulp is heated to a temperature from about 48°–52° C. to coagulate said finely particulate green material.

17. A process according to claims 11, 12 or 13 wherein the coarse particulate material is separated from the liquid portion and the residue heated to a temperature from about 48°–52° C. to coagulate said finely particulate green material.

18. A process according to claims 11, 12 or 13 wherein, after separation of said ribulose 1,5-diphosphate carboxylase, the liquid portion is acidified to at or below the isoelectric point of dissolved proteins to precipitate said proteins.

19. A process according to claim 18 wherein the pH is adjusted to within the range of pH 4.0–4.5.

20. A process according to claims 11, 12 or 13 wherein the leaf and stalk portions of the tobacco plants are converted to the pulp.

21. A process according to claims 11, 12 or 13 wherein a reducing agent is added to said plant material in an amount sufficient to suppress oxidation of amino acid substituent groups comprising part of the structure of proteins present in said liquid portion.

22. A process according to claim 21 wherein said reducing agent is 2-mercaptoethanol.

23. A process according to claim 21 wherein said reducing agent is added to the plant material prior to its conversion to said pulp.

24. A process according to claims 11, 12 or 13 wherein said ribulose 1,5-diphosphate carboxylase precipitates as octagonal crystals.

* * * * *